US008065768B2

(12) United States Patent
Graham et al.

(10) Patent No.: US 8,065,768 B2
(45) Date of Patent: *Nov. 29, 2011

(54) EQUIPMENT SUPPORT RAIL FOR HOSPITAL BED

(75) Inventors: Mark A. Graham, Loveland, OH (US); David C. Newkirk, Lawrenceburg, IN (US); Jonathan D. Turner, Dillsboro, IN (US); Christian H. Reinke, York, SC (US); Stephen R. Hamberg, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/603,820

(22) Filed: Oct. 22, 2009

(65) Prior Publication Data
US 2010/0095454 A1   Apr. 22, 2010

Related U.S. Application Data

(62) Division of application No. 11/185,046, filed on Jul. 20, 2005, now Pat. No. 7,624,463.

(60) Provisional application No. 60/598,530, filed on Aug. 3, 2004.

(51) Int. Cl.
*A61G 7/05* (2006.01)
*A61G 7/005* (2006.01)

(52) U.S. Cl. ........................ 5/658; 5/503.1; 5/600; 5/610

(58) Field of Classification Search ................ 5/81.1 R, 5/86.1, 425, 428–430, 503.1, 600, 610, 611, 5/613, 616–618, 658
See application file for complete search history.

(56) References Cited

U.S. PATENT DOCUMENTS

| 1,057,719 | A | * | 4/1913 | Farnsworth ........................ 5/11 |
| 1,208,979 | A | | 12/1916 | Kahre |
| 2,749,196 | A | | 6/1956 | Wolfe |
| 2,957,187 | A | | 10/1960 | Raia |
| 3,317,931 | A | | 5/1967 | Benoit et al. |
| 3,593,350 | A | | 7/1971 | Knight et al. |
| 3,709,372 | A | | 1/1973 | Alexander |
| 4,023,849 | A | | 5/1977 | Bethlen |
| 4,262,872 | A | | 4/1981 | Kodet |
| 4,558,857 | A | | 12/1985 | Heller |
| 4,592,104 | A | | 6/1986 | Foster et al. |
| 4,751,754 | A | | 6/1988 | Bailey et al. |
| 4,795,122 | A | | 1/1989 | Petre |

(Continued)

FOREIGN PATENT DOCUMENTS

DE      2803354      8/1979

(Continued)

OTHER PUBLICATIONS

USPTO Restriction Requirement for U.S. Appl. No. 11/185,046, Mail Date Sep. 27, 2007.

(Continued)

*Primary Examiner* — Robert G Santos
(74) *Attorney, Agent, or Firm* — Barnes & Thornburg LLP

(57) ABSTRACT

A patient support includes a lower frame, an upper frame supported above the lower frame, an equipment carrier coupled to the upper frame, and an actuator operable to adjust the orientation of the equipment carrier to compensate for the upper frame changing its orientation between the Trendelenberg and reverse Trendelenberg positions.

20 Claims, 6 Drawing Sheets

U.S. PATENT DOCUMENTS

| | | | |
|---|---|---|---|
| 4,862,529 | A | 9/1989 | Peck |
| 4,945,592 | A | 8/1990 | Sims et al. |
| 5,078,349 | A | 1/1992 | Smith |
| 5,306,109 | A | 4/1994 | Kreuzer et al. |
| 5,337,992 | A | 8/1994 | Pryor et al. |
| 5,344,169 | A | 9/1994 | Pryor et al. |
| 5,400,995 | A | 3/1995 | Boyd |
| 5,407,163 | A | 4/1995 | Kramer et al. |
| 5,454,126 | A | 10/1995 | Foster et al. |
| 5,527,289 | A | 6/1996 | Foster et al. |
| 5,647,491 | A | 7/1997 | Foster et al. |
| 5,682,631 | A | 11/1997 | Weismiller et al. |
| 5,745,936 | A | 5/1998 | Van McCutchen et al. |
| 5,987,670 | A | 11/1999 | Sims et al. |
| 6,109,572 | A | 8/2000 | Urban et al. |
| 6,375,133 | B1 | 4/2002 | Morrow |
| 6,390,311 | B1 | 5/2002 | Belokin |
| 6,585,206 | B2 * | 7/2003 | Metz et al. ............... 248/229.1 |
| 6,601,860 | B2 | 8/2003 | Potter |
| 6,619,599 | B2 | 9/2003 | Elliott et al. |
| 6,688,569 | B1 | 2/2004 | Weiss |
| 6,708,991 | B1 | 3/2004 | Ortlieb |
| 6,966,086 | B2 * | 11/2005 | Metz et al. ............... 5/510 |
| 7,065,812 | B2 | 6/2006 | Newkirk et al. |
| 7,216,382 | B2 | 5/2007 | Newkirk et al. |
| 7,624,463 | B2 * | 12/2009 | Graham et al. ............... 5/658 |
| 2003/0088920 | A1 | 5/2003 | Allen et al. |
| 2003/0093860 | A1 | 5/2003 | Kramer et al. |
| 2005/0000019 | A1 | 1/2005 | Newkirk et al. |
| 2006/0031989 | A1 | 2/2006 | Graham et al. |
| 2006/0207026 | A1 | 9/2006 | Newkirk et al. |
| 2007/0187559 | A1 | 8/2007 | Newkirk et al. |
| 2010/0095454 | A1 * | 4/2010 | Graham et al. ............... 5/503.1 |

FOREIGN PATENT DOCUMENTS

| | | |
|---|---|---|
| DE | 29518818 | 3/1996 |
| EP | 129735 | 1/1985 |

OTHER PUBLICATIONS

USPTO Non-Final Office Action for U.S. Appl. No. 11/185,046, Mail Date Jan. 11, 2008.

USPTO Non-Final Office Action for U.S. Appl. No. 11/185,046, Mail Date Sep. 5, 2008.

USPTO Final Office Action for U.S. Appl. No. 11/185,046, Mail Date Apr. 15, 2009.

USPTO Interview Summary for U.S. Appl. No. 11/185,046, Mail Date Jul. 6, 2009.

USPTO Notice of Allowance for U.S. Appl. No. 11/185,046, Mail Date Jul. 23, 2009.

\* cited by examiner

EQUIPMENT SUPPORT RAIL FOR HOSPITAL BED

CROSS-REFERENCE TO RELATED APPLICATIONS

This application is a divisional of U.S. Non-provisional patent application Ser. No. 11/185,046, filed on Jul. 20, 2005, now U.S. Pat. No. 7,624,463, and claims the benefit of U.S. Provisional Application Ser. No. 60/598,530, filed Aug. 3, 2004, which is hereby expressly incorporated by reference herein.

BACKGROUND OF THE INVENTION

The present disclosure relates to an equipment support rail for supporting patient care equipment, such as an infusion management system, adjacent to a patient support, such as a hospital bed.

Hospitalized patients often require patient care equipment to be in close proximity during hospital care. Such patient care equipment is typically supported on a patient care equipment support carried by a support structure, such as a service column, a hospital bed, and the like. Illustratively, the patient care equipment includes heart monitoring equipment, medical gas delivery equipment, infusion management systems, IV bags, patient monitors, equipment monitors, defibrillators, and the like, many of which directly connect to the patient via lines or tubes.

Many hospital beds are movable between a Trendelenberg position and a reverse Trendelenberg position. It is desirable to maintain the vertical orientation of the patient care equipment support carried by the hospital bed as the hospital bed moves between the Trendelenberg and reverse Trendelenberg positions.

SUMMARY OF THE INVENTION

The present invention comprises one or more of the following features or elements in the appended claims or combinations thereof.

A patient support apparatus may comprise a lower frame, an upper frame supported above the lower frame, a rail coupled to the upper frame, an equipment carrier coupled to the rail, and an actuator operable to maintain the orientation of the equipment carrier relative to the lower frame as the upper frame changes its orientation relative to the lower frame.

The upper frame may be configured to change its orientation between the Trendelenberg and reverse Trendelenberg positions. Illustratively, the actuator is operable to maintain the vertical orientation of the equipment carrier as the upper frame changes its orientation between the Trendelenberg and reverse Trendelenberg positions.

The equipment carrier may include first and second portions movably coupled to each other. The first portion may be coupled to the rail and the second portion may be coupled to the actuator so that the actuator can change the orientation of the second portion relative to the first portion to maintain the vertical orientation of the second portion as the upper frame changes its orientation relative to the lower frame.

The actuator may comprise a manually operable knob to change the orientation of the second portion relative to the first portion. The actuator may include a first threaded member having a first end coupled to the first portion and a second end coupled to the knob and a second threaded member coupled to the second portion and configured to threadably engage the first threaded member to move the second portion relative to the first portion in response to the rotation of the knob. The first threaded member may comprise a screw and the second threaded member may comprise a nut threadably engaging the screw.

The apparatus may comprise a socket coupled to the second portion. The socket may include an upwardly-extending bore to receive a downwardly-extending post of a patient care equipment support, such as an infusion management device ("IMD"). The actuator may be operable to maintain the vertical orientation of the IMD as the orientation of the upper frame changes between the Trendelenberg and reverse Trendelenberg positions.

The IMD may be supported by the rail, and the actuator may be operable to maintain the vertical orientation of the rail carrying the IMD as the upper frame changes its orientation. The rail may have a first portion pivotally coupled to the upper frame and a second portion pivotally coupled to the actuator. The actuator may comprise an electrically powered linear actuator that is coupled to the upper frame and coupled the second portion of the rail. The linear actuator may be controlled automatically to maintain the vertical orientation of the rail carrying the IMD as the orientation of the upper frame changes relative to the floor.

The rail may have an upper track surface facing downwardly and a lower track surface facing upwardly, and the equipment carrier may have at least one upper roller located below the upper track surface and riding on the upper track surface and at least one lower roller located above the lower track surface and riding on the lower track surface.

The upper and lower track surfaces may be convex and the upper and lower rollers may have concave circumferences. The upper and lower convex track surfaces may be received in the concave circumferences of the upper and lower rollers to maintain the equipment carrier on the rail.

A pair of mounting plates may be coupled to opposite ends of the rail to prevent the equipment carrier from falling off the ends of the rail. Each mounting plate may include a mounting bracket integrally formed therewith and configured to be coupled to the upper frame. The rail may be extruded.

Additional features which may comprise patentable subject matter will become apparent to those skilled in the art upon consideration of the following detailed description of illustrative embodiments exemplifying the best mode of carrying out the present invention as presently perceived.

BRIEF DESCRIPTION OF THE DRAWINGS

The detailed description particularly refers to the accompanying figures, in which.

DESCRIPTION OF THE ILLUSTRATIVE EMBODIMENTS

Figure 1:
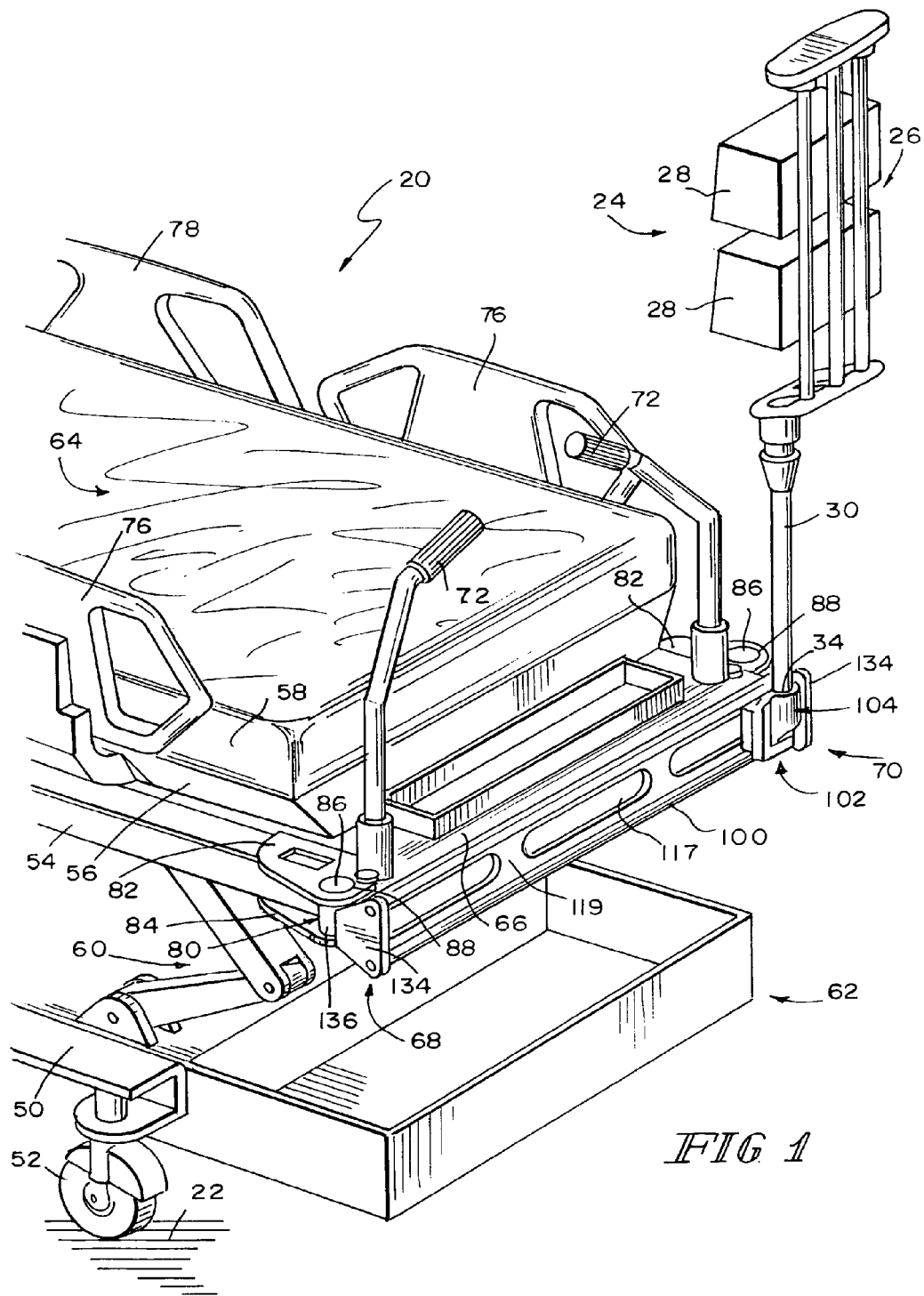
FIG. 1 is a perspective view of a patient support including a first embodiment of an equipment support rail having an equipment carrier for supporting a patient care equipment support.

FIG. 1 shows a patient support apparatus 20, such as a hospital bed, supported on a floor 22 of a hospital room. Apparatus 20 comprises a support rail 100 configured to support a patient care equipment support 24, such as an infusion management device (referred to herein as "IMD"). In FIG. 1, the illustrative apparatus 20 is a hospital bed and the illustrative patient care equipment support 24 is an IMD. However, it should be understood that the patient support apparatus 20 may very well comprise a stretcher, a surgery table, an ambulatory care chair, and the like. Likewise, it should be understood that the patient care equipment support 24 may very well be configured to support any type of patient care equipment such as, for example, one or more of the following: heart monitoring equipment, medical gas delivery equipment, patient monitors, equipment monitors, defibrillators, and the like, many of which directly connect to the patient via lines or tubes.

The equipment support 24 includes an equipment supporting portion 26 configured to support patient care equipment 28 and a downwardly-extending post 30 coupled to the equipment supporting portion 26. The post 30 has a lower tapered portion 34 configured for receipt in a socket 104 of an equipment carrier 102 which is supported by the rail 100. The equipment support 24 is transferable between the apparatus 20 and some other support structure, such as a service column.

Illustratively, the apparatus 20 includes a lower frame 50 supported on casters 52, an upper frame 54 supported above the lower frame 50, a deck 56 supported above the upper frame 54, and a mattress 58 supported on the deck 56. An elevation adjustment mechanism 60 connects the upper frame 54 to the lower frame 50. The upper frame 54 has a head end 62 and a foot end 64. The upper frame 54 includes a head-end frame member 66, which extends horizontally along the head end 62 of the upper frame 54 beyond the outer periphery of deck 56. The equipment support rail 100 is supported adjacent to the head-end frame member 66. An equipment carrier or carriage 102 is mounted on the rail 100 for movement therealong between opposite ends 68, 70 of the rail 100. As shown, for example, in FIGS. 2 and 3, the equipment carrier 102 includes a socket mount 124 having an upwardly-opening bore 125 for receiving the socket 104. The socket 104 is configured to releasably receive the lower tapered portion 34 of the post 30 of the equipment support 24. The carrier 102 may be configured to be lockable at any one of a plurality of locations along the rail 100. A pair of push handles 72 are coupled to the head-end frame member 66. The apparatus 20 includes a pair of side rails 76 near the head end 62 and a pair of side rails 78 near the foot end 64 to prevent a patient supported on the mattress 58 from rolling off the bed 20. The side rails 72, 74 are movable to a storage position below the deck 56.

The elevation mechanism 60 is driven by suitable actuators to raise and lower the upper frame 54 relative to the lower frame 50, and to change the angular orientation of the upper frame 54 relative to the lower frame 50 between a Trendelenberg position where the head end 62 of the upper frame 54 is below the foot end 64 of the upper frame 54 and a reverse Trendelenberg position where the head end 62 of the upper frame 54 is above the foot end 64 of the upper frame 54. U.S. Patent Application Publication No. US 2005/0000019 A1, titled "PATIENT CARE EQUIPMENT MANAGEMENT SYSTEM," filed Mar. 17, 2004, now U.S. patent Ser. No. 10/802,289, discloses an illustrative hospital bed and equipment support, and is incorporated by reference herein.

Figure 2:
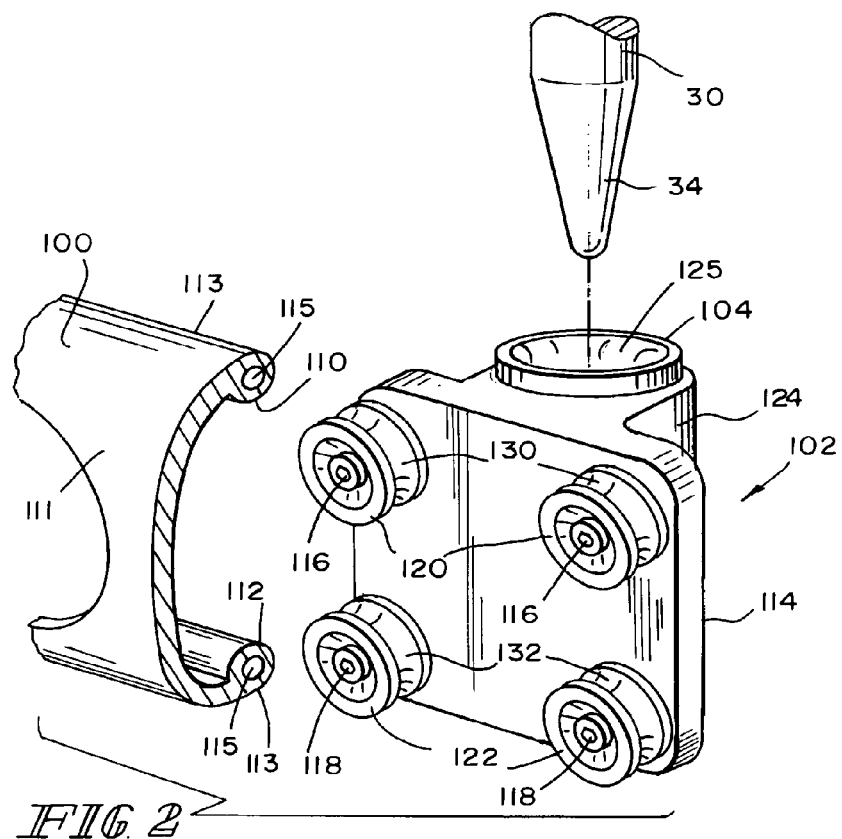
FIG. 2 is a perspective view of the equipment support rail and the equipment carrier of FIG. 1.
Figure 3:
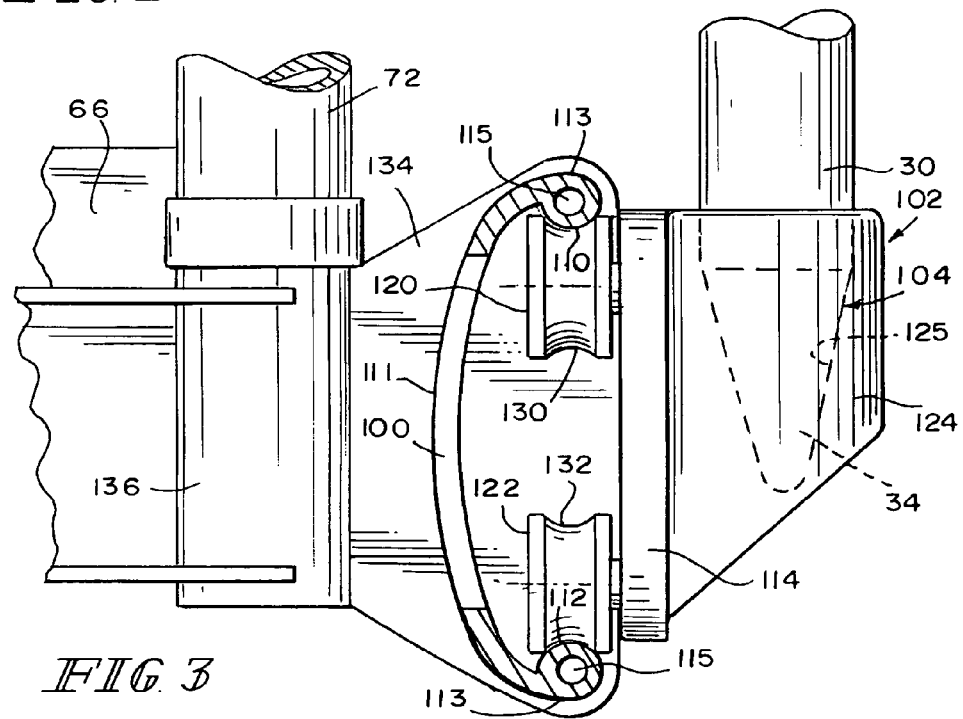
FIG. 3 is a cross sectional view of the equipment support rail and a side elevation view of the equipment carrier of FIGS. 1 and 2.

As shown in FIGS. 2 and 3, the rail 100 has an upper track surface 110 facing downwardly and a lower track surface 112 facing upwardly. The carrier 102 includes a roller mounting plate 114, a pair of upper rollers 120 rotatably mounted to the mounting plate 114 by respective pins 116, and a pair of lower rollers 122 rotatably mounted to the mounting plate 114 by respective pins 118. The upper rollers 120 are located below the upper track surface 110 and ride on the upper track surface 110. The lower rollers 122 are located above the lower track surface 112 and ride on the lower track surface 112. Illustratively, the upper and lower track surfaces 110, 112 are convex. The upper and lower rollers 120, 122 have complementary concave grooves 130, 132 along their respective circumferences. The receipt of the upper and lower convex track surfaces 110, 112 in the complementary concave grooves 130, 132 of the upper and lower rollers 120, 122 retains the carrier 102 on the rail 100. A pair of rail mounting plates 134 are coupled to the respective ends 68, 70 of the rail 100. The mounting plates 134 prevent the carrier 102 from falling off the ends 68, 70 of the rail 100.

Figure 10:
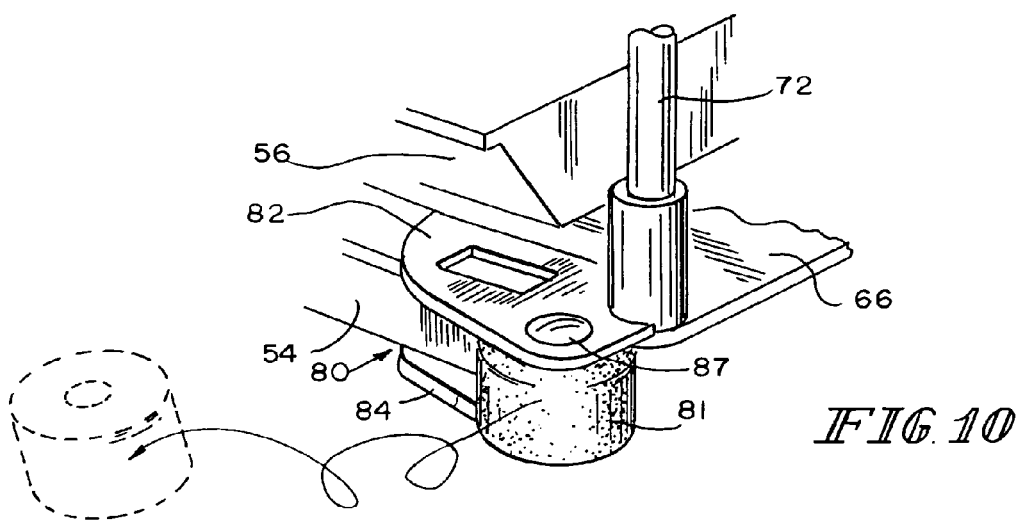
FIG. 10 is a perspective view showing a roller bumper coupled to the upper frame of the patient support.

As shown in FIG. 1, the mounting plates 134 are coupled to the head-end frame member 66 by a pair of mounting bosses 136 which are received in spaces 80 between respective upper and lower brackets 82, 84 attached to the head-end frame member 66. In some embodiments, roller bumpers 81 of the bed 20 are received in the spaces 80 as shown in FIG. 10. The roller bumpers 81 protect the bed 20 from accidental or incidental contact with the carts and the like. A fastener, such as a bolt 87, extends through openings 88 in the upper and lower brackets 82, 84 and through bores in the roller bumpers 81 to mount the roller bumpers 81 to the head-end frame member 66 of the upper frame 54. However, in the embodiment shown, for example, in FIGS. 1-3, the roller bumpers 81 are removed from the spaces 80 and replaced with the bosses 136 to support the mounting plates 134 of the rail 100. A fastener, such as a bolt 86, extends through the openings 88 in the upper and lower brackets 82, 84 and through bores in the bosses 136 to mount the rail 100 to the head-end frame member 66 of the upper frame 54. Illustratively, the rail 100 is extruded, and the mounting bosses 136 are integrally formed with the associated mounting plates 134.

In the illustrated embodiment, the rail 100 has convex track surfaces 110, 112, and the rollers 120, 122 have complementary concave grooves 130, 132. Alternatively, the rail 100 may have concave grooves and the rollers 120, 122 may have complementary convex track surfaces. Also, in the illustrated embodiment, the track surfaces 110, 112 and the complementary grooves 130, 132 have rounded cross sections. Alternatively, the track surfaces 110, 112 and the complementary grooves 130, 132 may have other suitable cross sections, such as v-shaped, rectangular, etc. In some embodiments, sliding elements may be substituted for the rollers 120, 122. In some other embodiments, the rollers 120, 122 may be dispensed with, and the equipment carrier 102 may ride directly on the rail 100.

As shown in FIGS. 1 and 2, the cross section of the rail 100 is generally C-shaped with an arcuate portion 111 interconnecting elongated cylindrical beads 113 which provide the track surfaces 110, 112. The mounting plates 134 couple to the opposite ends 68, 70 of the rail 100 by fasteners, such as screws, which are received in the hollow bores 115 of the beads 113 of the rail 100. To reduce the weight of the rail 100, a plurality of large openings 117 are formed in the arcuate portion 111 of the rail 100 creating small webs 119 extending between the openings 117. Also to reduce the weight, the cylindrical beads 113 are hollow.

Figure 4:
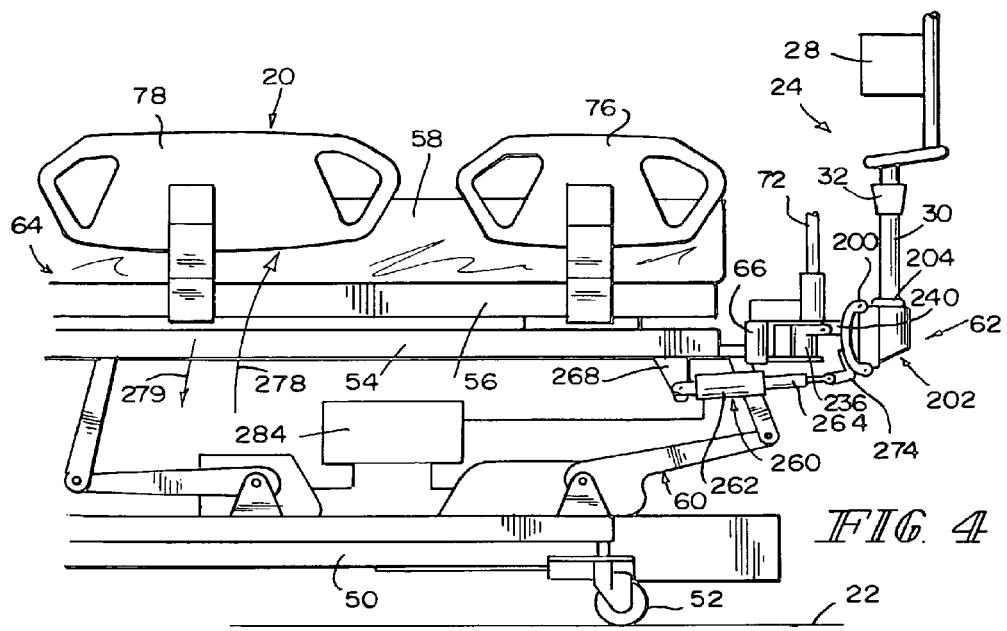
FIG. 4 is a side elevation view of a patient support including a second embodiment of an equipment support rail having an equipment carrier for supporting a patient care equipment support.
Figure 5:
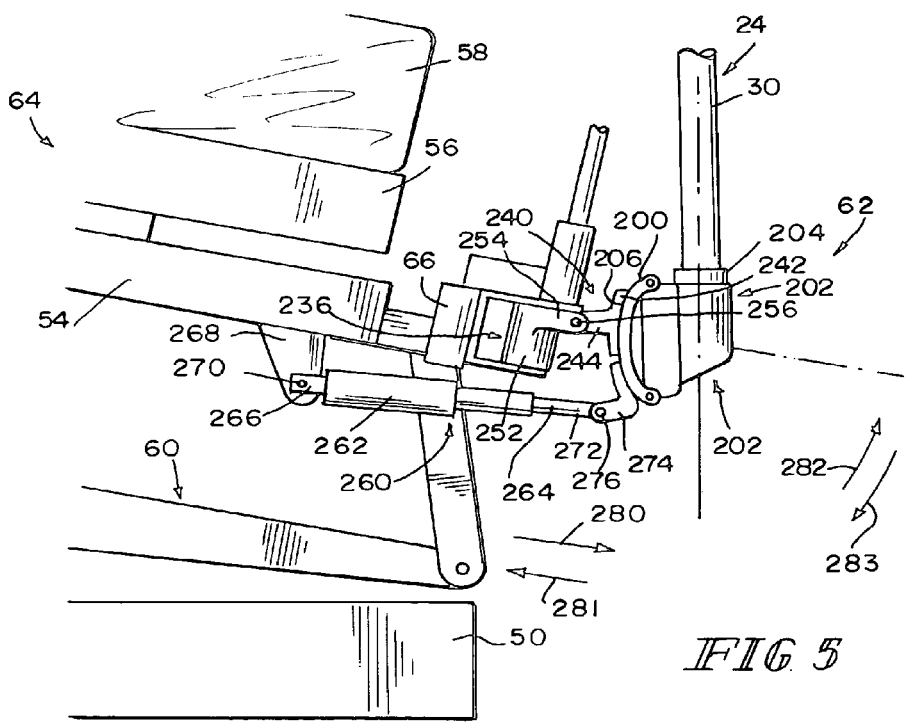
FIG. 5 is a side elevation view similar to FIG. 4 showing the patient support in the Trendelenberg position and a linear actuator extended to maintain the patient care equipment support in a vertical orientation.
Figure 8:
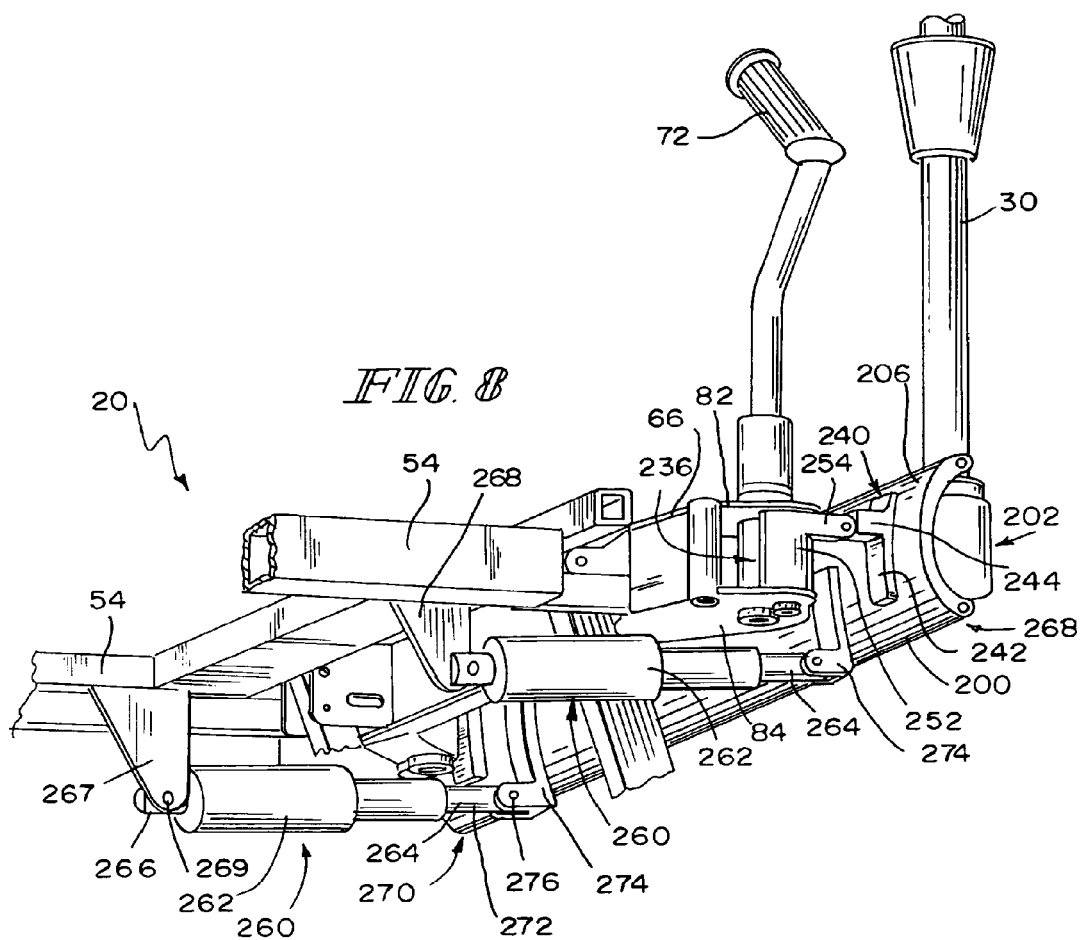
FIG. 8 is a perspective view of the patient support of FIGS. 4 and 5 showing a pair of actuators pivotally coupled to the equipment support rail and operable to tilt the equipment support rail relative to an upper frame of the patient support.

FIGS. 4, 5 and 8 illustrate a second embodiment of the support rail 100 and the equipment carrier 102. Like elements of the two embodiments have generally similar reference numbers. Thus, in the second embodiment, numeral 200 designates the support rail and numeral 202 designates the equipment carrier. The rail 200 is pivotally mounted to the head-end frame member 66 of the upper frame 54 by a pair of brackets 240 near the opposite ends 268, 270 of the rail 200. Each rail mounting bracket 240 has a first generally vertical rail mounting portion 242 secured to the rearwardly-facing wall 206 of the rail 200 and a second generally horizontal flange portion 244 extending rearwardly from the first rail mounting portion 242. A pair of frame mounting bosses 236 are coupled to the head-end frame member 66 in a manner similar to the manner in which the mounting bosses 136 are coupled to the head-end frame member 66. Thus, the bosses 236 are received in the spaces 80 between respective upper and lower brackets 82, 84 attached to the head-end frame member 66 and coupled to the brackets 82, 84 by respective bolts. Each frame mounting boss 236 has a first generally vertical frame mounting portion 252 and a second generally horizontal flange portion 254 extending forwardly from the first frame mounting portion 252. The rearwardly-extending portions 244 of the rail mounting brackets 240 are pivotally coupled to the forwardly-extending portions 254 of the frame mounting blocks 236 by pins 256. The rail 200 may include stops to prevent the carrier 202 from falling off the ends 268, 270 of the rail 200. Such stops are rail mounting plates (not shown) which attach to the ends of the rail 200. Illustratively, the rail 200 is extruded.

A pair of actuators 260, one near each end 268, 270 of the rail 200, are operable to maintain the vertical orientation of the equipment support 24 as the upper frame 54 changes its angular orientation between the horizontal position shown in FIG. 4, the Trendelenberg position shown in FIG. 5 where the head end 62 of the upper frame 54 is below the foot end 64 of the upper frame 54 and the reverse Trendelenberg position (not shown) where the head end 62 of the upper frame 54 is above the foot end 64 of the upper frame 54. Each actuator 260 comprises a housing 262 and a piston 264 that retracts into and extends out of the housing 262. The foot end 266 of the housing 262 is pivotally coupled to a bracket 267 by a pin 269. The bracket 267 is mounted to the underside of the upper frame 54. The head end 272 of the piston 264 is pivotally coupled to a bracket 274 by a pin 276. The bracket 274 is mounted to the rearwardly-facing wall 206 of the rail 200. As the upper frame 54 pivots in a clockwise direction 278 as shown in FIG. 4, the piston 264 extends out of the housing 262 in a forward direction 280 as shown in FIG. 5 and the rail 200 pivots in a counterclockwise direction 282 to maintain the vertical orientation of the equipment support 24. As the upper frame 54 pivots in a counterclockwise direction 279, the piston 264 retracts into the housing 262 in a rearward direction 281 and the rail 200 pivots in a clockwise direction 283 to maintain the vertical orientation of the equipment support 24. Thus, the piston 264 is movable into and out of the housing 262 to maintain the vertical orientation of the equipment support 24 as the angular orientation of the upper frame 54 changes between the horizontal, Trendelenberg and reverse Trendelenberg positions. Illustratively, the actuator 260 is an electrically powered linear actuator of the type manufactured by Linak. Although two actuators 260, one near each end 268, 270 of the rail 200, are shown in the embodiment of FIGS. 4 and 5, one actuator near the middle of the rail 200 may very well be used to pivot the rail 200 to compensate for the change in the orientation of the upper frame 54.

In some embodiments, a sensor (not shown) is provided to determine the vertical orientation of the equipment support 24. A control circuit 284, illustrated diagrammatically in FIG. 5, drives the actuators 260 in response to an output from the sensor to maintain the vertical orientation of the equipment support 24 as the upper frame 54 changes its orientation between the horizontal, Trendelenberg and reverse Trendelenberg positions. Alternatively, a sensor (not shown) is provided to determine the angular orientation of the upper frame 54, instead of the equipment support 24. A control circuit, such as a circuit 284, drives the actuators 260 in response to an output from the sensor to maintain the vertical orientation of the equipment support 24 as the upper frame 54 changes its angular orientation.

In further embodiments, actuators 260 and the actuators associated with the elevation adjustment mechanism 60 have sensors, such as potentiometers, which produce signals that correspond to the amount of extension or retraction of the pistons of the respective actuators. In such embodiments, the circuit 284 controls the actuators 260 by calculating the appropriate amount of extension or retraction of the actuators 260 needed to maintain the vertical orientation of the equipment support 24 based on the angle of inclination of the deck 56 as determined by the circuit 284 from the signals provided by the actuators of the elevation adjustment mechanism 60. In some embodiments, the actuators 260 are controlled with a pair of manually-operable push buttons, one to rotate the rail 200 in the counterclockwise direction 282 and one to rotate the rail 200 in the clockwise direction 283. The user operates the push buttons to maintain the vertical orientation of the equipment support 24.

Figure 6:
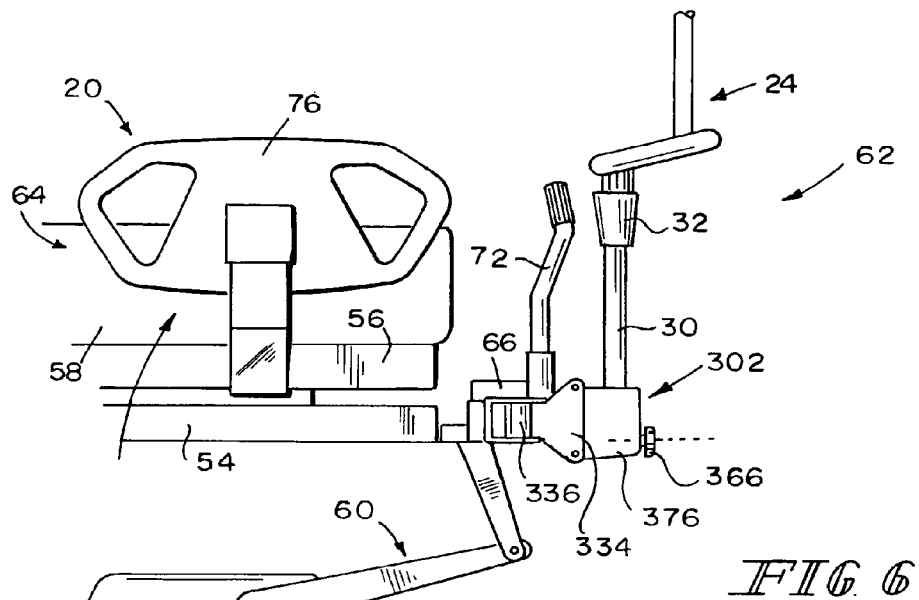
FIG. 6 is a side elevation view of a patient support including a third embodiment of an equipment support rail having an equipment carrier for supporting a patient care equipment support.
Figure 9:
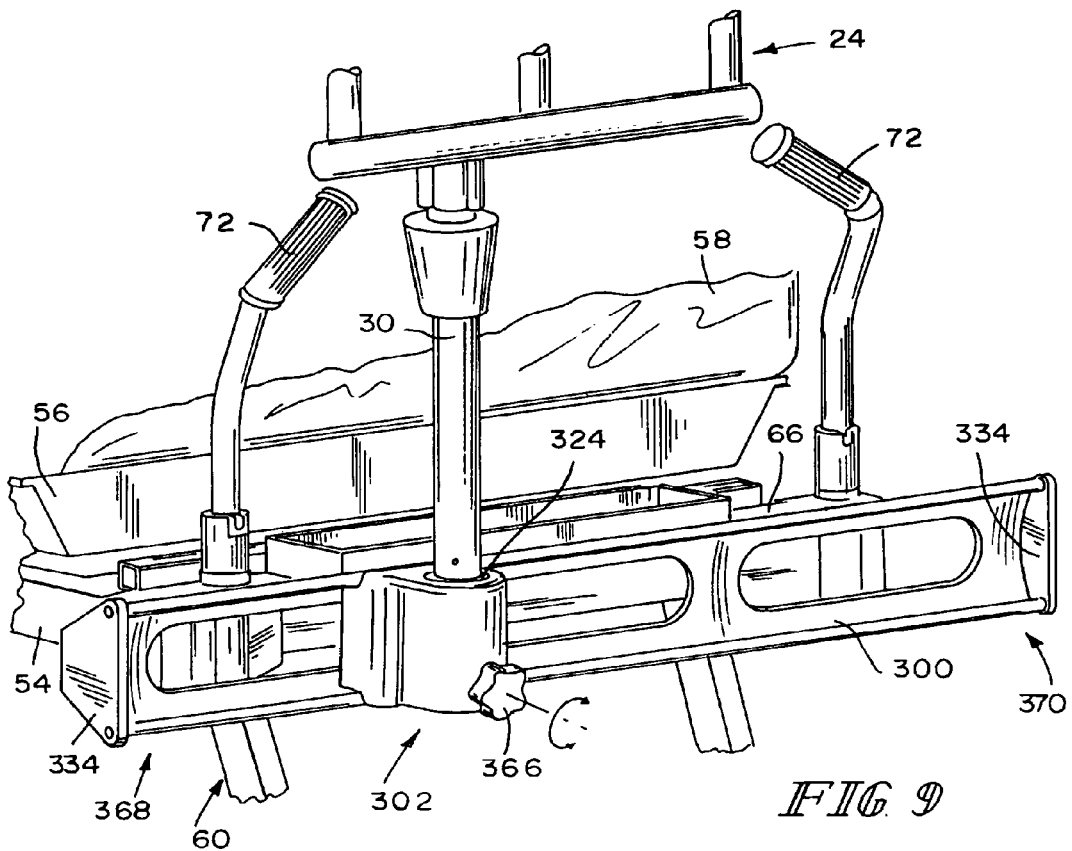
FIG. 9 is a perspective view of the patient support of FIGS. 6 and 7 showing a knob coupled to the equipment carrier and operable to tilt the equipment carrier relative to the equipment support rail.

FIGS. 5, 6 and 9 show a third embodiment of the support rail 100 and the equipment carrier 102. Like elements of the various embodiments have generally similar reference numbers. Thus, in the third embodiment, numeral 300 designates the support rail and numeral 302 designates the equipment carrier. The rail 300 has an upper track surface 310 facing downwardly and a lower track surface 312 facing upwardly. The carrier 302 includes a roller mounting plate 314, a pair of upper rollers 320 pivotally mounted to the mounting plate 314, and a pair of lower rollers 322 pivotally mounted to the mounting plate 314. The upper rollers 320 are located below the upper track surface 310 and ride on the upper track surface 310. The lower rollers 322 are located above the lower track surface 312 and ride on the lower track surface 312. The upper and lower track surfaces 310, 312 are convex. The upper and lower rollers 320, 322 have complementary concave grooves 330, 332 along their respective circumferences. The receipt of the upper and lower convex track surfaces 310, 312 in the complementary concave grooves 330, 332 of the upper and lower rollers 320, 322 retains the carrier 302 on the rail 300.

A pair of rail mounting plates 334 are coupled to the respective ends 368, 370 of the rail 300. The mounting plates 334 prevent the carrier 302 from falling off the ends 368, 370 of the rail 300. The mounting plates 334 are coupled to the upper frame 54 by a pair of mounting bosses 336. The mounting bosses 336 are coupled to the head-end frame member 66 in a manner similar to the manner in which the mounting bosses 136 are coupled to the head-end frame member 66. Thus, the bosses 336 are received in the spaces 80 between respective upper and lower brackets 82, 84 attached to the head-end frame member 66 and bolted thereto. Illustratively, the rail 300 is extruded, and the mounting bosses 336 are integrally formed with the associated mounting plates 334.

The carrier 302 includes a socket mount 324 pivotally coupled to the roller mounting plate 314 by pins 326. The socket mount 324 has a body portion having an upwardly-opening bore for receiving the socket 104. A pair of upper flange portions 340 extend forwardly from the mounting plate 314. A pair of flange portions 342 extend downwardly from the socket mount 324. The upper flange portions 340 are spaced apart to define a socket mount-receiving space in which the socket mount 324 is pivotally mounted by the pins 326.

Figure 7:
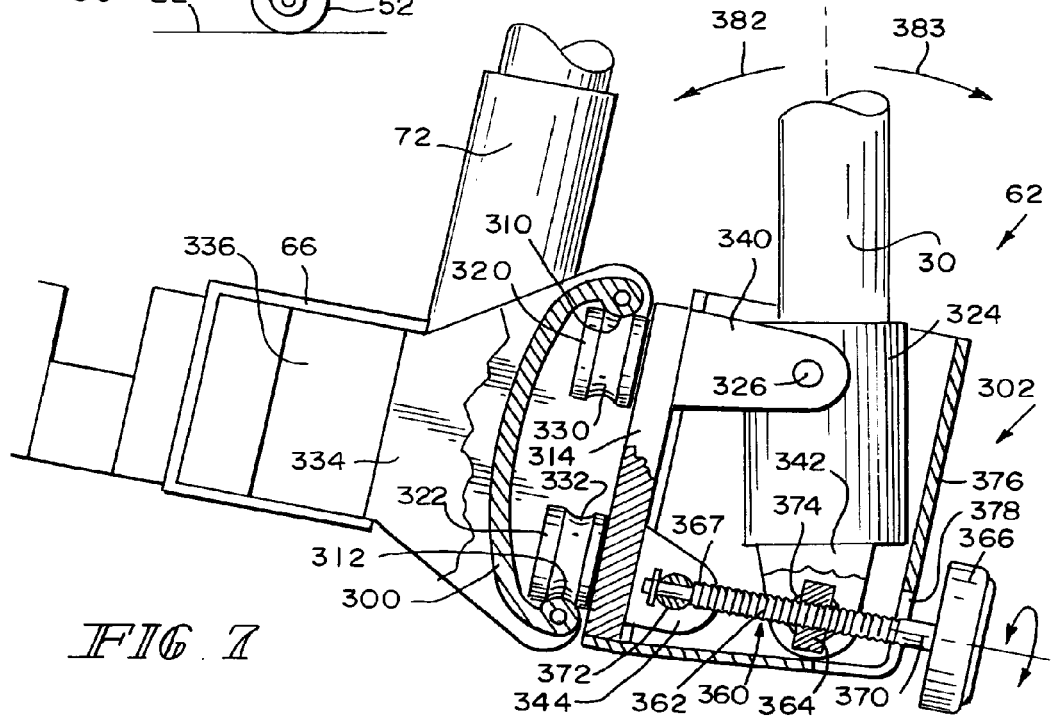
FIG. 7 is a cross sectional view showing the patient support in the Trendelenberg position and a knob rotated manually to maintain the patient care equipment support in a vertical orientation.

An actuator 360 comprises a first threaded member, such as a screw 362, a second threaded member, such as a nut 364, and a manually operable knob 366. The screw 362 has first and second ends 367, 369. The first end 367 of the screw 362 is coupled to a pin 372 which is pivotally mounted between a pair of lower flange portions 344 extending forwardly from the roller mounting plate 314. The knob 366 is coupled to the second end 369 of the screw 362 to turn the screw 362. The screw 362 is threadably received in the nut 364 which is pivotally mounted between the downwardly-extending flange portions 342 of the socket mount 324 by pins 374. As the knob 366 is turned, the screw 362 threads into and out of the nut 364 depending on the direction of rotation of the knob 366. As the screw 362 threads into the nut 364, the socket mount 324 pivots in a clockwise direction 383 as shown in FIG. 7. As screw 362 threads out of the nut 364, the socket mount 324 pivots in a counterclockwise direction 382. Thus, the knob 366 is rotatable to maintain the vertical orientation of the equipment support 24 as the angular orientation of the upper frame 54 changes between the horizontal, Trendelenberg and reverse Trendelenberg positions.

As best shown in FIGS. 6 and 9, a cosmetic cover 376 is provided in the illustrated embodiment. The cover 376 shields from view most of the socket mount 324, flanges 340-344, screw 362, nut 364, pins 372 and 374, but is open on the top to permit the post 30 of the equipment support 24 to be inserted into the socket 104. Furthermore, the cover 376 has an opening 378 through which the end 369 of the screw 362 extends to support the knob 366 outside the interior of the cover 376.

Although the invention has been described in detail with reference to certain illustrative embodiments, variations and modifications exist with the scope and spirit of this disclosure as described and defined in the following claims.

The invention claimed is:

1. A patient support apparatus comprising:
a lower frame;
an upper frame movably supported above the lower frame by a support;
a rail pivotally coupled to the upper frame and configured to maintain its angular orientation with respect to the lower frame as the angular orientation of the upper frame changes between a first angular orientation and a second angular orientation with respect to the lower frame; and
an equipment carrier including a socket mount configured to receive an equipment support, the equipment carrier being configured to movably engage the rail to move the equipment support from a first position to a second position with respect to the rail.

2. The patient support apparatus of claim 1 further comprising an actuator coupled to the frame and the rail, wherein the actuator is configured to maintain the angular orientation of the rail with respect to the lower frame as the angular orientation of the upper frame changes with respect to the lower frame.

3. The patient support apparatus of claim 1, wherein the rail includes a track with an upper track surface and a lower track surface, the upper track surface facing the lower track surface.

4. The patient support apparatus of claim 3, wherein at least one of the upper track surface and the lower track surface is convexly shaped.

5. The patient support apparatus of claim 3, wherein the equipment carrier is movably retained between the upper track surface and the lower track surface.

6. The patient support apparatus of claim 1, wherein the equipment carrier includes at least one wheel configured to engage the rail.

7. The patient support apparatus of claim 6, wherein the wheel includes a concave portion configured to engage a convex portion of the rail.

8. The patient support apparatus of claim 1, wherein the socket mount is pivotable with respect to the equipment carrier to maintain the angular orientation of the socket mount with respect to the lower frame as the angular orientation of the equipment carrier changes with respect to the lower frame.

9. The patient support apparatus of claim 1, wherein the equipment carrier includes an actuator movably coupled thereto and engaging the socket mount, the actuator being configured to change the angular orientation of the socket mount with respect to the equipment carrier.

10. The patient support apparatus of claim 9, wherein the actuator includes a threaded shaft configured to engage a portion of the socket mount, the socket mount moving along the threaded shaft as the threaded shaft is rotated.

11. The patient support apparatus of claim 1, wherein the socket mount includes an opening therein configured to receive and removably retain an end of the equipment support.

12. The patient support apparatus of claim 1, wherein the equipment support is an infusion management device.

13. The patient support apparatus of claim 1, wherein the upper frame includes a pair of end mounts coupled thereto, the rail being coupled to the pair of end mounts.

14. The patient support apparatus of claim 13, wherein the pair of end mounts are configured to couple with roller bumpers when the rail is not coupled to the end mounts.

15. A person-support apparatus comprising:
a lower frame;
an upper frame movably supported above the lower frame by a support;
a rail coupled to the upper frame; and
an equipment carrier movably coupled to the rail, the equipment carrier including a socket and an orientation adjusting mechanism configured to maintain the angular orientation of the socket with respect to the lower frame as the angular orientation of the upper frame changes with respect to the lower frame.

16. The person-support apparatus of claim 15, wherein the upper frame is configured to move between a Trendelenburg position and a reverse Trendelenburg position with respect to the lower frame.

17. The person-support apparatus of claim 15, wherein the rail is movably coupled to the upper frame and is configured to maintain an angular orientation with respect to the lower frame as the angular orientation of the upper frame changes.

18. The person-support apparatus of claim 15 further comprising an actuator coupled to the upper frame and the rail, the actuator being configured to change the angular orientation of the rail with respect to the upper frame.

19. The person-support apparatus of claim 15, wherein the adjustment mechanism includes a threaded shaft configured to rotatably engage a portion of the socket to change the angular orientation of the socket with respect to the equipment carrier.

20. A person-support apparatus comprising:
a lower frame;
an upper frame movably supported above the lower frame by a support;
a rail coupled to the upper frame; and
an equipment carrier movably coupled to the rail, the equipment carrier including a socket and an orientation adjusting mechanism configured to maintain the angular orientation of the socket with respect to a reference plane as the angular orientation of the equipment carrier changes with respect to the reference plane.

* * * * *